United States Patent
Brugger et al.

(10) Patent No.: US 6,514,177 B1
(45) Date of Patent: *Feb. 4, 2003

(54) INHALING APPARATUS COMPRESSOR WITH IMPROVED DIAPHRAGM ASSEMBLY

(75) Inventors: Stephan Brugger, Starnberg (DE); Erich Hertl, Gilching (DE); Andreas Lintl, Starnberg (DE); Matthias Remke, Starnberg (DE)

(73) Assignee: Pari GmbH Spezialisten fur effektive Inhalation, Starnberg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/741,768

(22) Filed: Nov. 5, 1996

(51) Int. Cl.[7] .................................. A63B 23/18
(52) U.S. Cl. .......................... 482/13; 604/65
(58) Field of Search ..................... 482/113; 128/205.24, 128/204.18, 204.28, 205.13, 205.18, DIG. 17, DIG. 13; 261/DIG. 27; 417/413.1; 92/100; 604/65, 66, 67

(56) References Cited

U.S. PATENT DOCUMENTS

| | | | | |
|---|---|---|---|---|
| 2,846,139 A | * | 8/1958 | Blount | 92/100 X |
| 3,364,870 A | * | 1/1968 | Quatredeniers | 417/413.1 X |
| 4,433,966 A | * | 2/1984 | Krumm | 92/100 X |
| 4,571,160 A | * | 2/1986 | King | 417/413.1 X |
| 4,993,925 A | * | 2/1991 | Becker | 417/413.1 |
| 5,554,014 A | * | 9/1996 | Becker | 417/413.1 |

FOREIGN PATENT DOCUMENTS

EP  0010943  * 5/1980 ................. 92/100

* cited by examiner

Primary Examiner—Manuel Mendez
Assistant Examiner—Lalita M. Hamilton
(74) Attorney, Agent, or Firm—Merchant & Gould P.C.

(57) ABSTRACT

A diaphragm assembly for the diaphragm pump of an inhaling apparatus compressor contains a flexible diaphragm 1, 21 with a first opening 2, 22, a lower diaphragm disc 6, 26, with a second opening 8, 28, and an upper diaphragm disc 14, 38 with a third opening 16, 40, said diaphragm discs 6, 14, 26, 38 having a smaller diameter than the flexible diaphragm 1, 21, and a securement member 18, 44, for clamping the diaphragms 1, 21, between the lower diaphragm discs 6, 26 and the upper diaphragm discs 14, 38, said securement member 18, 44 being guided through the first, second and third opening 2, 12, 16, 22, 28, 40 and being in engagement with a diaphragm drive device.

Figure 1:
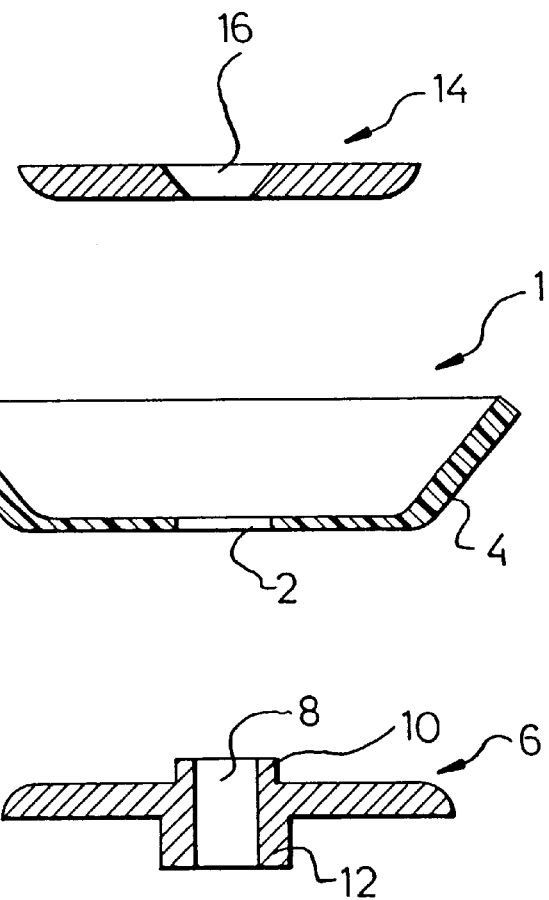

For the improvement of the operational behavior and production ability, it is proposed that on the outer periphery of the flexible diaphragms 1, 21, a strip-shaped portion 4, 24 be bent towards the axis of the securement member 18, 44 and along the upper rim of the second opening 8, 28 a stop member 10, 30, be formed, against which the inside rim of the first opening of the flexible diaphragm 1, 21 can abut.

10 Claims, 4 Drawing Sheets

INHALING APPARATUS COMPRESSOR WITH IMPROVED DIAPHRAGM ASSEMBLY

SPECIFICATION

The present invention relates to a diaphragm assembly for a diaphragm pump of an inhaling apparatus compressor with the features of the main claim of patent claim 1.

Figure 7:
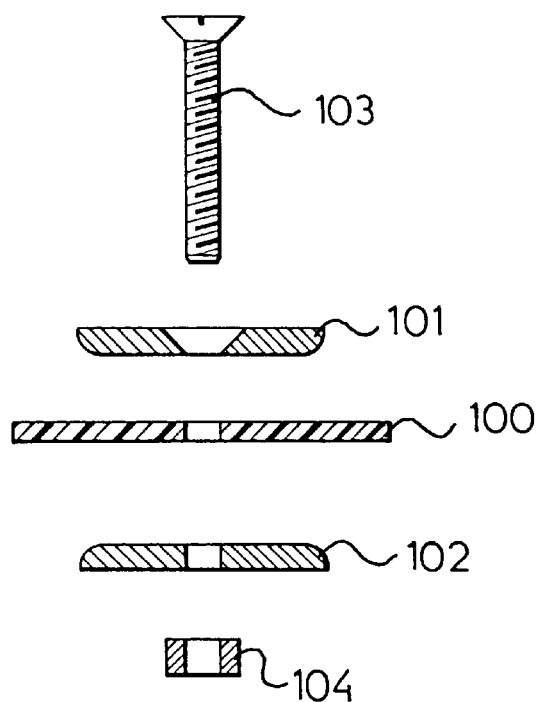

Such a diaphragm assembly is known from the German Patent DE 86 26 979.9. As shown in FIG. 7, a flat diaphragm 100 is clamped between an upper diaphragm disc 101 and a lower diaphragm disc 102. This takes place with the aid of a countersunk screw 103 which is guided through openings in the center of the upper diaphragm disc, the diaphragm and the lower diaphragm disc so that they can be screwed with a connecting rod for actuation of the diaphragm. An intermediate ring 104 is generally inserted between the lower diaphragm disc and the connecting rod.

Figure 8:
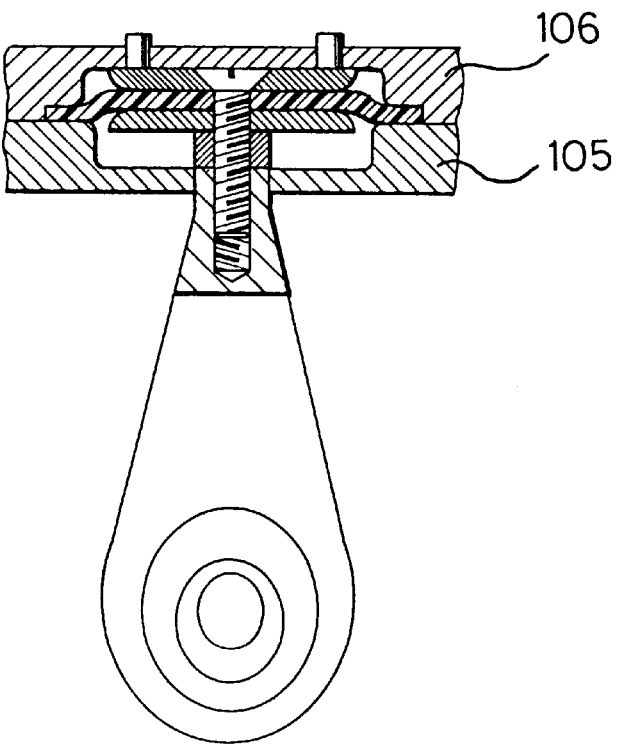

As shown in FIG. 8, such a diaphragm assembly is used in a diaphragm compressor which is formed from a compressor housing with a housing lower member 105 and a housing upper member 106. A circulating groove is provided in the housing upper member 106 which receives the outer rim of the flexible diaphragm. The diaphragm is held in its position inside the groove by pressing between the housing lower member and the housing upper member. The two diaphragm discs which abut against the upper and lower side of the diaphragm are rigid against distortion so that the diaphragm therebetween can merely be elastically deformed in its free rim region.

Such diaphragm assemblies are used for conveying and compressing fluid and gaseous media, for example in inhaling apparatuses. It is generally endeavoured to achieve a construction for the largest possible range of use so that with a rigidly predetermined drive performance a highest possible pressure and weight rate of flow must be achieved. This is generally achieved by adaptation of the clearance volume directly over the clamped rim of the diaphragm and by an enlargement of the unstiffened rim region of the flexible diaphragm.

However, on account of the enlarged rim region of the flexible diaphragm, the noise development also increases, which is especially critical in the case of use in inhaling apparatuses. Care must be taken here that the therapeutical effect for the patient to be treated is not impaired by an excessively high noise development.

Furthermore, as shown in FIG. 7, the diaphragm assembly according to the prior art involves not inconsiderable problems with respect to production, which remain unsolved until now. If, as explained above, the diaphragm is clamped between the upper diaphragm disc and the lower diaphragm disc with the aid of a countersunk screw, dependent on the force with which the countersunk screw is tightened different radii of the diaphragm occur after clamping, and thus different pretensions in the diaphragm material.

It is moreover difficult to achieve a uniform clamping of the flexible diaphragm in different diaphragm assemblies, and high tolerances occur in the production of the diaphragm assemblies. In particular in the cases in which the diaphragm is clamped especially rigidly the screw must be tightened with a high force, which is especially strenous and fatiguing for the personnel. This mode of procedure is as a whole intricate and time-consuming, so that on account of the increasing quantities in which such diaphragm assemblies are manufactured there is an acute necessity for action.

The object on which the present invention is based consists in providing a diaphragm assembly which can be simply produced with improved production tolerances and which simultaneously reveals favorable operating properties and has a long life.

According to the invention, this object is solved in a diaphragm assembly for a diaphragm pump of the initially described type in that on the outer periphery of the flexible diaphragm a ring-shaped portion is bent towards the axis of the securement member, and along the upper rim of the second opening a stop member is formed against which the inside rim of the first opening of the flexible diaphragm abuts.

An important advantage of the invention lies in the fact that on account of the bending of the rim portion of the flexible diaphragm, a shaping of the flexible diaphragm is achieved from the very beginning which is necessary for a regular operation of the diaphragm assembly, so that when clamping the flexible diaphragm between the upper and lower diaphragm discs, considerably less force needs to be applied, with the result that the personnel is relieved and the production process accelerated.

A further important advantage of the invention is that the flexible diaphragm abuts against a stop member on the inner side of its opening. This leads to the fact that upon alignment of the upper and lower diaphragm discs and the flexible diaphragm practically no more deviations can occur and the production tolerances can be considerably improved.

When, as described above, the outer rim of the flexible diaphragm is pressed into a groove of the housing upper member between the housing upper member and housing lower member, the unstiffened rim region of the flexible diaphragm projects toroidally into the clearance volume so that this is reduced. Accordingly, the diaphragm assembly according to the invention permits an improved noise behaviour since due to the reduced clearance volume less noise disturbances occur as a whole.

The unstiffened rim region of the flexible diaphragm projecting toroidally into the clearance volume of the diaphragm compressor can also roll off directly upon an up and down movement of the flexible diaphragm. On account of this rolling off procedure, the deformation in the flexible diaphragm occurring during the up and down movement can be reduced, so that the life of the flexible diaphragm is considerably lengthened. Furthermore, the toroidal course of the unstiffened rim region of the flexible diaphragm effects a continuous change of the clearance volume which leads to the fact that the operating pressure during compression of fluid or gaseous media is increased and the maximum pressure during operation reduced. This also results in a flat characteristic curve.

In a further especially preferred embodiment of the diaphragm assembly according to the invention, at least one centralizing groove for the flexible diaphragm is provided in the lower diaphragm disc between the outer periphery and the stop member, the flexible diaphragm comprising at least one holding ring in a corresponding manner. In this embodiment, the alignment of the individual components of the diaphragm assembly to one another is further improved, since independent of the force with which the flexible diaphragm is clamped between the upper and the lower diaphragm disc, a deformation of the flexible diaphragm in the area of the clamping position is excluded.

In an especially advantageous development of the diaphragm assembly according to the invention, it is provided that the lower diaphragm disc has a torus on its outer periphery. This advantageously favors the above-described rolling off procedure during the up and down movement of the flexible diaphragm.

Figure 2:
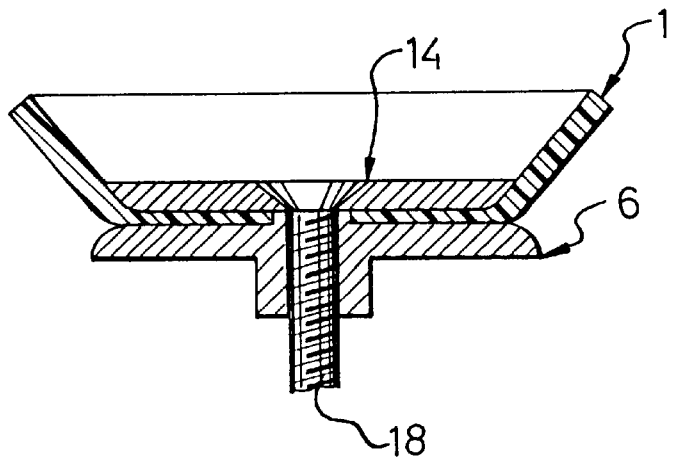
Figure 3:
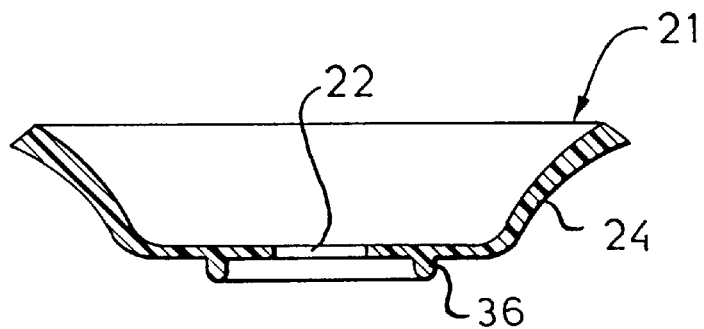
Figure 3:
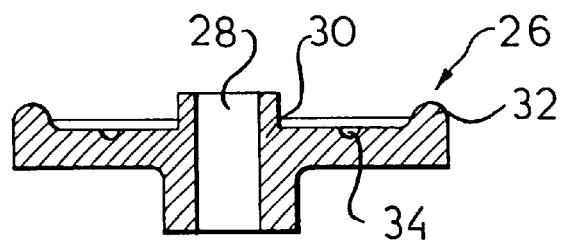
Figure 4:
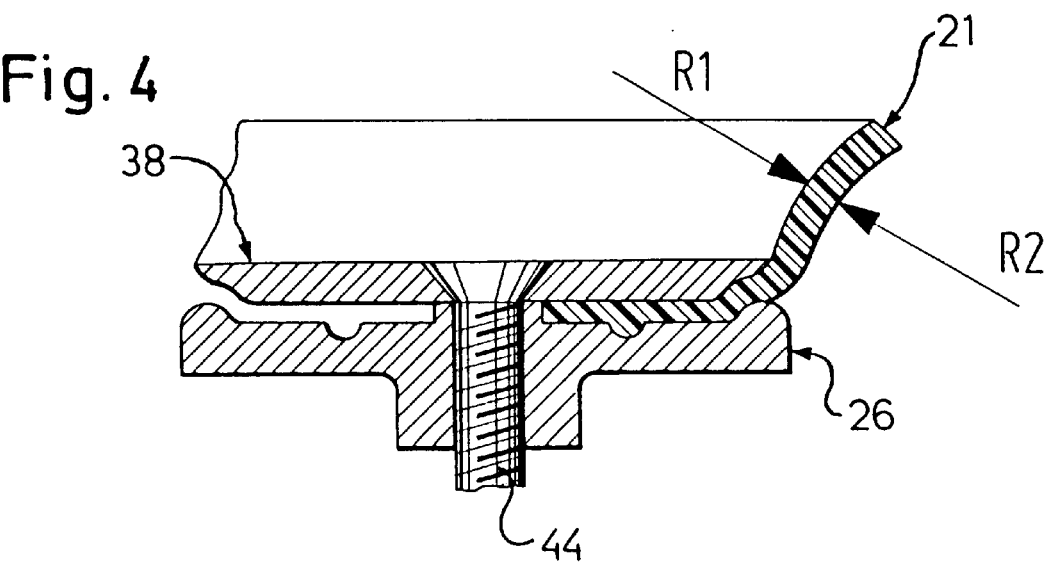
Figure 5:
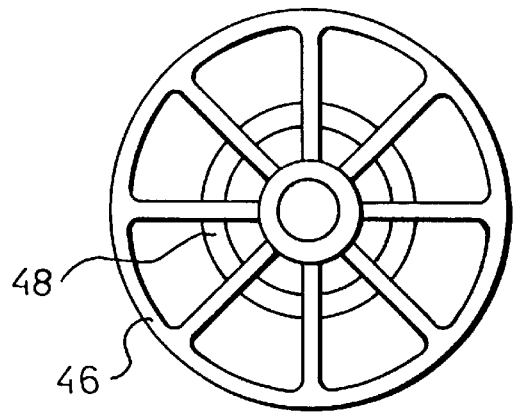
Figure 6A:
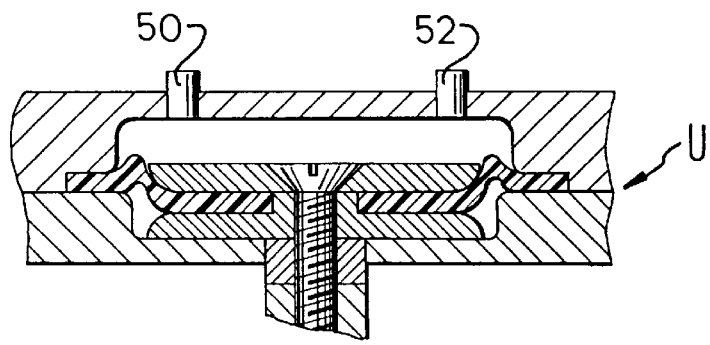
Figure 6B:
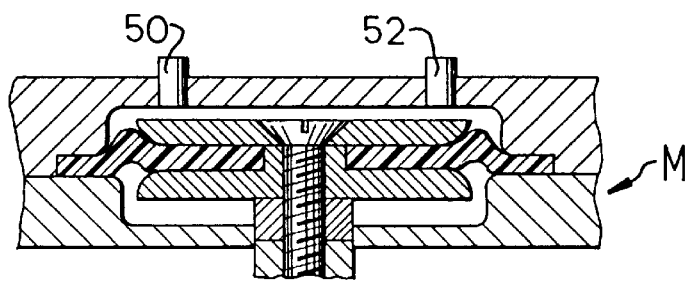
Figure 6C:
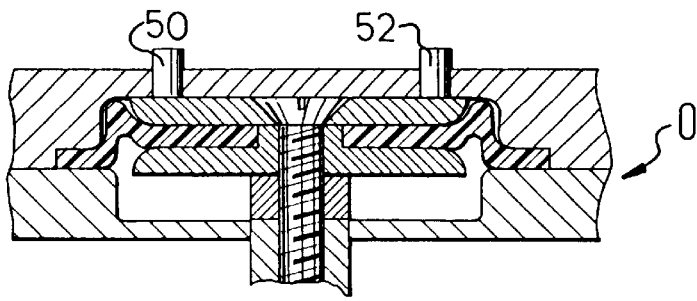

Further features and advantages of the invention can be taken from the following description of several embodiments which are represented in the drawing; these show:

FIG. 1 a cross-section through the first embodiment of the diaphragm assembly according to the invention in the explosion representation;

FIG. 2 a cross-section through the first embodiment of the diaphragm assembly in mounted form;

FIG. 3 a cross-section through the second embodiment of the diaphragm assembly according to the invention in the explosion representation;

FIG. 4 a partial cross-sectional view through the second embodiment of the diaphragm assembly according to the invention in mounted form;

FIG. 5 a plan view on an embodiment of a lower diaphragm disc according to the invention:

FIGS. 6a to 6c respectively a cross-sectional view of the first embodiment of the diaphragm assembly according to the invention after installation in a diaphragm compressor according to a lower, middle and upper operating position;

FIG. 7 a cross-sectional view through a diaphragm assembly according to the prior art in explosion representation; and FIG. 8 a cross-sectional view through a diaphragm compressor according to the prior art with the known diaphragm assembly.

A first embodiment of the diaphragm assembly is shown in FIG. 1. A flexible diaphragm 1 reveals a first opening 2 in its center. Furthermore, the flexible diaphragm is constructed in a substantially frustum shape so that a strip-shaped portion 4 is bent inwardly at its outer periphery. The flexible diaphragm 1 is held at its lower side by a lower diaphragm disc 6 with a second opening 8. The diameter of the lower diaphragm disc 6 is selected such that this extends up to the strip-shaped portion 4 of the flexible diaphragm 1. Moreover a stop member 10 is formed along the upper rim of the second opening 8, against which the inner rim of the first opening 2 of the flexible diaphragm 1 abuts. A projecting portion 12 is formed along the lower rim of the second opening 8 of the lower diaphragm disc 6, so that the lower diaphragm disc 6 surrounds as a whole a hollow-cylindrical portion in a flange-like manner.

The flexible diaphragm 1 is held at its upper side by an upper diaphragm disc 14, the diameter of which essentially conforms with the diameter of the lower diaphragm disc. The upper diaphragm disc 14 comprises a third opening 16 in its center.

A securement member 18 can be guided through the first, second and third opening 2, 8, 16 so that the flexible diaphragm is clamped between the upper diaphragm disc 14 and the lower diaphragm disc 6, as shown in FIG. 2.

On account of the abutment of the flexible diaphragm 1 against the stop member 10, a correct alignment of the individual members to one another is possible, without any special additional measures being required during production. Moreover, on account of the fact that the flexible diaphragm is of frustum shape with a laterally bent strip-shaped portion, a shaping by especially rigid clamping of the flexible diaphragm 1 between the upper diaphragm disc 14 and the lower diaphragm disc 6 is not necessary.

Accordingly, in the production of the diaphragm assembly according to the first embodiment, a low clamping power is already sufficient upon assembly of the components, so that the frustum shape of the flexible diaphragm 1 does not alter. Accordingly, considerably lower production tolerances can be kept. Moreover, on account of the lower rotational forces when joining the components and due to the stop member 10 for simple alignment of the components to one another, the personnel is considerably relieved.

A second embodiment of the diaphragm assembly according to the invention is shown in FIG. 3 and 4. In this embodiment a flexible diaphragm 21 is essentially chalice-shaped and provided with a first opening 22 in its center. The strip-shaped portion 24 of the flexible diaphragm 21 is curved at its upper side with a first radius R1 and at its lower side with a second radius R2, the two radii being in a ratio of about 1.125. Due to this different curvature a shaping of the strip-shaped portion 24 of the flexible diaphragm 21 is achieved which is rounded off towards the outside.

The flexible diaphragm 21 is held at the lower side by a lower diaphragm disc 26 with a second opening 28. Along the upper rim of the second opening 28 a stop member 30 is formed, against which the inner rim of the first opening 22 of the flexible diaphragm 21 abuts. Moreover, the lower diaphragm disc 26 comprises a torus 32 on its outer periphery. Between the torus 32 and the stop member 30 a centralizing groove 34 is provided, the flexible diaphragm 21 being provided at the relevant position with a circular holding projection 36.

The flexible diaphragm 21 is held at the upper side by an upper diaphragm disc 38 with a third opening 40. The upper diaphragm disc 38 comprises a round recess 42 on the lower side of its outer periphery, the curvature radius of which is adapted to the outer radius of the torus 32 of the lower diaphragm disc 26.

The upper diaphragm disc 38, the flexible diaphragm 21 and the lower diaphragm disc 26 are joined together by a securement member 44, for example a countersunk screw.

In addition to the advantages already explained with respect to the first embodiment, the second embodiment permits a practically faultless alignment of the individual components to each other. This is due to the additionally provided centralizing groove 34 and the additional holding projection 36 of the flexible diaphragm 21.

Furthermore, the torus 32 of the lower diaphragm disc 26 together with the round recess 42 of the upper diaphragm disc 38 and the construction of the strip-shaped portion 24 of the flexible diaphragm 21 with different curvature radii R1, R2 on the upper and lower side leads to an especially advantageous toroidal formation of the unstiffened rim region of the diaphragm assembly.

As shown in FIG. 5, for the reduction of the weight of the diaphragm assembly, the lower diaphragm disc can be constructed as a thin plate-wheel 46 which is provided with an additional stiffening ring 48 to improve the shape rigidity. With the reduced weight of the spoked wheel 46, lower masses need to be moved upon operation of the diaphragm assembly. As a whole the oscillations occurring and the noise disturbances connected therewith are reduced, which is especially significant for the use of the diaphragm assembly according to the invention in inhaling apparatuses.

The mode of functioning of the diaphragm assembly according to the invention should be described in the following on the basis of FIG. 6a to 6c.

The flexible diaphragm 1 or 21, respectively, of the diaphragm assembly is clamped after installation in a diaphragm compressor into a groove of a housing upper member between this housing upper member and the housing lower member. As shown in FIG. 6a, the unstiffened rim region of the diaphragm 1, 21 projects toroidally into the clearance volume of the diaphragm compressor. As shown by a comparison of FIGS. 6a, 6b and 6c, this isk the case both in the lower, and in the center and upper operating point U, M, 0 of the diaphragm assembly.

Accordingly, during the operation the flexible diaphragm 1, 21 is not deformed throughout by the up and down movement of the connecting rod for driving the diaphragm assembly, as known in the prior art, but a rolling off takes place at the position of deformation.

This rolling off process reveals considerable advantages in practical operation. Since the flexible diaphragm 1, 21 is not continuously deformed throughout, its working life is increased. Moreover, on account of the forming out of the flexible diaphragm 1, 21 according to the invention, a continually changing clearance volume can be achieved. This leads to an increased operating pressure and a reduced maximum pressure for the medium to be compressed which is suctioned into the clearance volume during the downward movement of the diaphragm assembly via an inlet opening 50 and then output through the output opening 52 upon the subsequent upward movement of the diaphragm assembly from a lower operating position U to an upper operating position 0.

The rolling off process additionally replaces cubic capacity, so that a larger dimensioning of the diaphragm assembly and a resultant larger dimensioning of a diaphragm pump is avoided. This is especially significant with use of the diaphragm assembly according to the invention in an inhaling apparatus which is to be realized with the smallest possible dimensions.

What is claimed is:

1. A diaphragm pump for supplying gas for an inhaling apparatus, comprising:

upper and lower housing members defining a chamber therebetween;

a flexible diaphragm having an outer edge and a first opening defining an inner periphery, the outer edge of the diaphragm being held between the upper and lower housing members;

a lower diaphragm disc having a second opening;

an upper diaphragm disc having a third opening, each of the lower and upper diaphragm discs having a diameter smaller than the diameter of the diaphragm, the diaphragm being held between the lower and upper diaphragm discs with the inner periphery of the diaphragm abutting a stop member;

a securing member extending through the first, second and third openings to clamp the diaphragm between the lower and upper diaphragm discs;

a diaphragm drive device for driving the lower and upper discs and the diaphragm in a reciprocating manner;

wherein the diaphragm is shaped so that, when the outer edge of the diaphragm is not held between the upper and lower housing members, a first portion of the diaphragm outside the periphery of the upper diaphragm disc extends in the direction of the upper diaphragm disc, and when the diaphragm is held between the upper and lower housing members, the first portion of the diaphragm forms a substantially toroidal protrusion extending in the direction of the upper disc member, the protrusion being present throughout the reciprocating movement of the diaphragm.

2. A diaphragm pump as claimed in claim 1, wherein the diaphragm is substantially frustum-shaped.

3. A diaphragm pump as claimed in claim 1, wherein the diaphragm is substantially chalice-shaped.

4. A diaphragm pump as claimed in claim 1, wherein the securing member is a countersunk screw and the third opening is countersunk to accept the countersunk screw.

5. A diaphragm pump as claimed in claim 1, wherein the lower diaphragm disc comprised a protrusion surrounding the second opening and extending from a lower surface of the lower diaphragm disc.

6. A diaphragm pump as claimed in claim 1, wherein the lower diaphragm disc comprises a toroidal protrusion extending in the direction of the upper diaphragm disc at an outer peripheral portion.

7. A diaphragm pump as claimed in claim 1, wherein an upper surface of the lower diaphragm disc is provided with a groove and the a lower surface of the diaphragm is provided with a protrusion that cooperates with the groove.

8. A diaphragm pump as claimed in claim 6, wherein a lower surface of the upper diaphragm disc is provided with a recessed peripheral portion adapted to the radius of curvature of the toroidal protrusion of the lower diaphragm disc.

9. A diaphragm pump as claimed in claim 3, wherein an upper surface of the first portion of the diaphragm has a cross-sectional radius of curvature R1 and a lower surface of the first portion of the diaphragm has a cross-sectional radius of curvature R2, with the ratio of R1 to R2 being about 1.125.

10. A diaphragm pump as claimed in claim 1, wherein the lower diaphragm disc is formed as a spoked wheel with a reinforcing ring.

* * * * *